United States Patent
Hoegerle et al.

(10) Patent No.: US 12,197,979 B2
(45) Date of Patent: Jan. 14, 2025

(54) MEDICAL INSTRUMENT HAVING AN INSTALLED TRANSPONDER MODULE, AND MEDICAL TRANSPONDER COMMUNICATION SYSTEM

(71) Applicant: Aesculap AG, Tuttlingen (DE)

(72) Inventors: Roland-Alois Hoegerle, Tuttlingen (DE); Frederick Lenzenhuber, Tuttlingen (DE); Ralf Pfister, Trossingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/012,340

(22) PCT Filed: Jun. 22, 2021

(86) PCT No.: PCT/EP2021/066911
§ 371 (c)(1),
(2) Date: Dec. 22, 2022

(87) PCT Pub. No.: WO2021/259894
PCT Pub. Date: Dec. 30, 2021

(65) Prior Publication Data
US 2023/0252257 A1      Aug. 10, 2023

(30) Foreign Application Priority Data
Jun. 26, 2020   (DE) ............ 10 2020 116 932.9

(51) Int. Cl.
*G06K 19/04*   (2006.01)
*A61B 90/98*   (2016.01)
*G06K 19/02*   (2006.01)

(52) U.S. Cl.
CPC ............ *G06K 19/045* (2013.01); *A61B 90/98* (2016.02); *G06K 19/022* (2013.01)

(58) Field of Classification Search
CPC .................................................. G06K 19/045
See application file for complete search history.

(56) References Cited

U.S. PATENT DOCUMENTS

| 7,722,531 B1 | 5/2010 | Boche |
| 9,033,251 B2 | 5/2015 | Weisshaupt et al. |
| (Continued) | | |

FOREIGN PATENT DOCUMENTS

| DE | 102016121478 A1 | 5/2018 |
| DE | 102019122349 A1 | 2/2021 |
| (Continued) | | |

OTHER PUBLICATIONS

Search Report received in German Application No. 10 2020 116 932.9 dated Mar. 25, 2021, with translation, 7 pages.
(Continued)

*Primary Examiner* — Joseph H Feild
*Assistant Examiner* — Pameshanand Mahase
(74) *Attorney, Agent, or Firm* — Christopher A. Rothe; CM Law

(57) ABSTRACT

A medical instrument and a medical transponder communication system. The medical instrument has an instrument body, which has a prepared depression or opening in an instrument body surface, and an installed transponder module having: a transponder, preferably an RFID transponder, particularly preferably a glass transponder, a housing which has an upper side and a lower side and in which the transponder is accommodated and which is provided and designed to be installed or inserted into the prepared depression or opening in the medical instrument with its lower side facing towards the depression so that the lower side is set back relative to the upper side and the instrument body surface, and a screen that is signal-opaque to electromagnetic waves and has a signal-transparent screen opening. The
(Continued)

transponder is spaced from and set back relative to the screen towards the lower side.

21 Claims, 5 Drawing Sheets

(56) References Cited

U.S. PATENT DOCUMENTS

| | | | | |
|---|---|---|---|---|
| 2006/0145871 | A1* | 7/2006 | Donati | A61B 90/98 340/539.1 |
| 2006/0232417 | A1* | 10/2006 | August | G06K 19/07703 340/572.1 |
| 2009/0267765 | A1* | 10/2009 | Greene | G06K 7/0008 340/568.1 |
| 2013/0186243 | A1* | 7/2013 | Harper | B25B 23/0035 29/446 |
| 2014/0131454 | A1 | 5/2014 | Weisshaupt et al. | |
| 2016/0128798 | A1 | 5/2016 | Bovet et al. | |
| 2018/0256287 | A1* | 9/2018 | Bosisio | A61C 5/42 |
| 2019/0377993 | A1 | 12/2019 | Nadig et al. | |

FOREIGN PATENT DOCUMENTS

| | | |
|---|---|---|
| EP | 2929853 A2 | 10/2015 |
| EP | 3193284 A1 | 7/2017 |
| WO | 2015177538 A1 | 11/2015 |
| WO | 2021032782 A1 | 2/2021 |
| WO | 2021259894 A1 | 12/2021 |

OTHER PUBLICATIONS

Search Report received in International Application No. PCT/EP2021/066911 dated Oct. 5, 2021, with translation, 7 pages.
Written Opinion received in International Application No. PCT/EP2021/066911 dated Oct. 5, 2021, with translation, 16 pages.

* cited by examiner

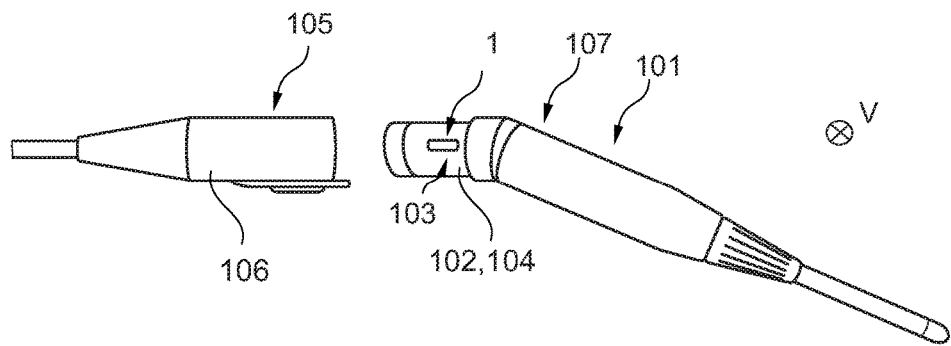
Fig. 12
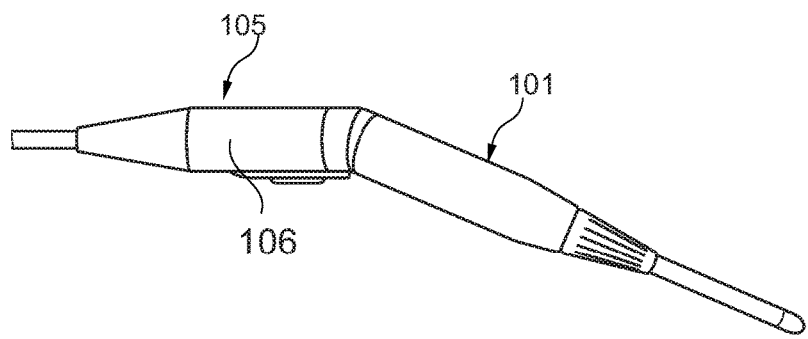
Fig. 13
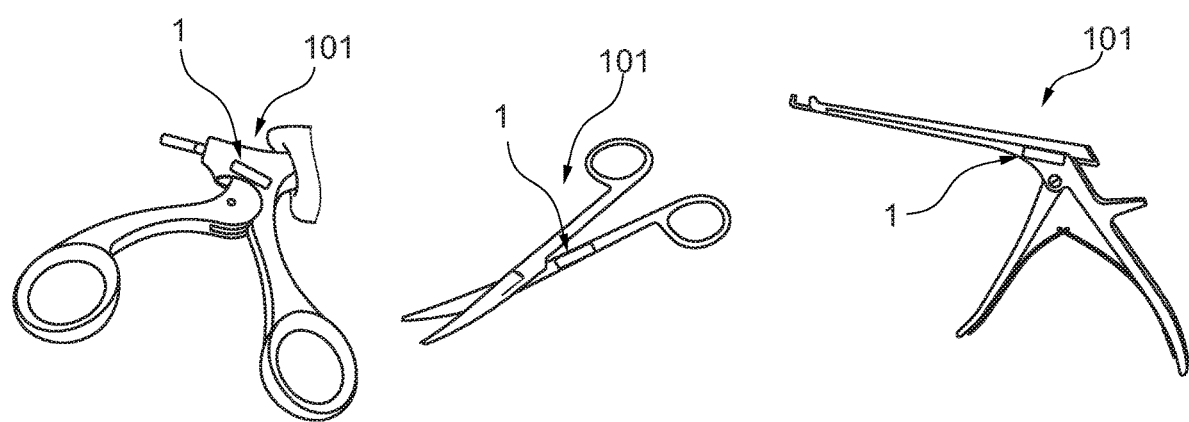
Fig. 14
Fig. 15
Fig. 16

MEDICAL INSTRUMENT HAVING AN INSTALLED TRANSPONDER MODULE, AND MEDICAL TRANSPONDER COMMUNICATION SYSTEM

CROSS-REFERENCE TO RELATED APPLICATIONS

This application is the United States national stage of International Application No. PCT/EP2021/066911, filed Jun. 22, 2021, and claims priority to German Application No. 10 2020 116 932.9, filed Jun. 26, 2020. The contents of International Application No. PCT/EP2021/066911 and German Application No. 10 2020 116 932.9 are incorporated by reference herein in their entireties.

FIELD

The invention relates to a medical instrument with a transponder installation module/transponder insertion module, wherein the transponder installation module comprises a transponder adapted to receive and/or transmit electromagnetic waves, in particular data signals. In addition, the invention relates to a medical transponder communication system/transponder system for communication or respectively for reading out and/or writing to a transponder installation module.

BACKGROUND

Assemblies with transponders or (medical) marking elements with RFID transponders or RFID tags are known from the prior art, which are used in particular for equipping surgical instruments. With the help of the RFID transponders attached to the surgical instruments, it is possible to identify, track and manage such an instrument. In particular, specific information of the instrument can be read out.

For example, EP 3 193 284 A1 discloses a medical marking element for equipping surgical instruments, which can be subsequently attached to the surface side of a surgical instrument. The marking element has a ring-shaped metal frame with a non-conductive cover, in the interior space of which an RFID transponder/RFID tag is inserted. An outer side of the metal frame is attached to the surgical instrument in a predetermined position, in particular by welding.

Likewise, WO 2015/177 538 A1 discloses a box-shaped assembly with an RFID transponder, which can be subsequently attached to the surface side of a metal frame of a surgical instrument. A cover is made of an electromagnetically permeable material.

One disadvantage of the prior art is that transponders, in particular passive transponders, have to be arranged at a short distance from a reading and writing device due to their short (signal-related/signaling) transmission range. In particular, this applies to NFC (Near Field Communication) RFID tags. For this reason, in the case of conventional transponders/RFID tags, it is often only possible to attach the RFID tags subsequently to an exposed and easily accessible external surface of a medical instrument in order to keep the distance between the transponder and the read-out device to a minimum. Care must be taken to ensure that the external surface provided for this purpose is located at an instrument site that has only minor disadvantages in terms of instrument handling and yet at the same time ensures sufficient transmission quality or sufficient reception.

In addition, transmission, reception or transmission power are significantly influenced by the components or structures surrounding the transponder. This also affects the (signal-related) reliability of a transmission of the transponder. In particular, however, a maximum possible distance to a reading and/or writing device changes so that, depending on the structure of the instrument and a location where an RFID tag is attached, a readout is no longer possible or at least not possible with sufficient reliability. The geometric mounting situation of an RFID marking element and thus of an RFID chip of the transponder has an essential effect on this maximum distance and varies from instrument to instrument, so that safe, reliable and predictable handling is not provided by marking elements of the prior art.

Therefore, when developing a design of a medical instrument, an RFID marking element as well as an environment of an RFID tag always have to be considered and find their way into the design, since this is the only way to ultimately ensure that a correspondingly suitable surrounding structure for the transponder is available. This makes it difficult to develop a medical instrument independently of the transponder. Since approval of medical products is a lengthy and very expensive process, both existing and new medical products face a particularly high hurdle with the corresponding challenge of adaptation.

In addition to the signal-related problems, the prior art also has the following disadvantages. Although such RFID marking elements are comparatively small components, the marking elements with RFID transponders attached subsequently in the prior art form additional attack surfaces for contamination and are also a hindrance when handling the medical instruments. RFID marking elements additionally applied to the surface side may also form gaps and crevices in which germs can accumulate. Also, due to the design of the marking elements and attachment to a medical instrument, irreversible attachment, in particular welding, is unavoidable and makes necessary replacement more difficult in the event of a defect or a planned change of the transponder. Furthermore, due to their harp edges, externally attached marking elements always carry a risk of tearing open a surgical glove and the patient as well as user damage.

The manufacture and installation of a marking element, in particular via welding, is also very complex and in some cases not even possible for some medical instruments, since no suitable materials of a surface are available for welding or since the intended mounting surfaces are not suitable. In particular, the parts of a housing or respectively of a holder of the RFID marking element always have to be made of metal in order to enable attaching and welding on, which limits the choice of suitable materials for a design. In addition, there are specifications from an approval of medical instruments, which in particular require a repeatable production and assembly of the RFID marking element. Metallic surfaces also shield RFID marking elements and reduce their accessibility.

SUMMARY

It is therefore the object of the present invention to eliminate or at least reduce the disadvantages of the prior art and in particular to provide a medical device, in particular a medical instrument, with a transponder installation module as well as a transponder communication system, which ensures a reliability of a signal-technical/signal communication and improves reception or reception power and/or transmission power of a transponder, in particular with respect to a distance to a reading and writing device. Furthermore, cleanability, sterilizability as well as good and safe handling of a medical instrument as well as a transponder installation module shall be improved. The development, manufacture, assembly, maintenance, repair and replacement of a medical instrument as well as of a transponder installation module are also to be improved. In case of service, the transponder installation module can be changed quickly.

In other words, it is in particular the object of the invention to provide a medical instrument that ensures good and safe handling with respect to both the instrument property and the data transmission property of the transponder. A further object preferably consists in good cleanability and/or sterilizability of the medical instrument.

The core of the present invention substantially lies in improving reception of a transponder and, in particular, a possible distance to an external reading and/or writing device, via a structurally and geometrically prefabricated, unitary transponder installation module/inserted transponder module/container for a transponder/an assembly of a transponder, with a received and position-fixed transponder, in particular in the form of a glass tag, and a screen with predefined geometric dimensions, which is specially arranged with respect to the transponder. The transponder installation module is adapted via its housing to be installed or inserted into the prepared depression or opening of the medical device, in particular of the medical instrument, so that this independent unit of the transponder installation module can be inserted into both existing and new medical instruments and already by itself fulfills the requirements for data communication through its predefined structure. The medical instrument itself only requires a predefined depression or opening for insertion.

The transponder installation module as an assembly has a structure-defining housing which securely holds and supports the transponder, in particular a glass tag, in a fixed position, and which also holds the screen or the reinforcing screen in a fixed position relative to the transponder. The housing itself is in particular signal-permeable and preferably has no or only little influence on a (signal-technical) reception of the transponder or on an electromagnetic interaction. The housing may be configured in particular with regard to good cleanability and sterilizability, and further with regard to installation or insertion into the medical instrument. The screen, which is made of a signal-impermeable material or a material that is not permeable to electromagnetic waves, at least for a certain frequency range, is completely different. The screen has an essential influence on an electromagnetic interaction between the transponder and the upper side of the transponder installation module and is in particular configured and adapted to bundle and/or amplify electromagnetic signals or electromagnetic waves between the upper side of the transponder installation module and the transponder.

This design optimizes the transponder installation module as a unit and significantly improves reception and transmission to or respectively from the transponder to the upper side. As a result, communication between a (transponder) reading and/or writing device that is arrangeable in the region of the upper side or of the instrument body surface is also improved, so that safe and reliable reading and/or writing of the transponder is ensured by the design of the transponder installation module itself, even over greater distances.

Specifically, the transponder installation module thus has a transponder, preferably an RFID transponder, also referred to as an RFID tag or RFID label, particularly preferably a glass transponder, also referred to as a glass tag. The transponder is provided for and adapted to receive and/or transmit (electromagnetic) waves or signals. The transponder is thus a contactless radio communication device that picks up incoming signals and automatically answers or forwards them. The transponder may be an active transponder or a passive transponder. Furthermore, the transponder installation module has a housing/transponder holder/transponder carrier with an upper side and a lower side opposite to and facing away from the upper side. The housing is provided and configured to receive the transponder in a fixed position between the upper side and the lower side and is further provided and configured to be installed or inserted into the prefabricated or prepared depression or sink or cavity or opening of a medical device, in particular of the instrument body surface of the medical instrument with its lower side facing in the direction of the depression, so that its lower side is set back relative to the upper side of the transponder installation module and in particular to a surface of a medical device, preferably the instrument body surface of the medical instrument.

A prepared depression or opening of the medical device, in particular of the medical instrument, may serve, for example, as a usual or standardized longitudinal groove with, in particular, rounded edges and/or ends. A prepared depression or opening has in particular in its place a direction of a depression perpendicular to the surface or to the instrument body surface, respectively. For example, a prepared depression or opening may be incorporated at a freely selectable location on a medical instrument via a milling tool, in particular a slot milling cutter, perpendicular to an instrument body surface there, wherein the transponder installation module can then be inserted into the prepared depression or opening, in particular via a press fit/force fit. In this way, a press fit can be realized. In particular, the prepared depression has a constant depth relative to the (instrument body) surface.

According to the invention, the transponder installation module has an electromagnetically (signal) impermeable screen/reinforcement screen with a screen opening, in particular in the centrally arranged. The screen/aperture thus has a material which is impermeable to electromagnetic waves, in particular in the range of radio frequencies and/or medium wave and/or short wave and/or ultra-short wave. In particular, this may be a highly conductive metallic material. Preferably, the screen comprises metal or even consists entirely of metal, in particular stainless steel. Thus, the screen forms a signal-impermeable frame for the screen opening and a shield or respectively a reflector screen and only the screen opening itself with its special geometry and its dimensions is provided to let a signal or respectively electromagnetic waves pass.

Furthermore, the screen is specially arranged relative to the transponder. Specifically, the transponder is spaced apart from the screen and set back in the direction of the lower side of the transponder installation module. With this arrangement it is achieved that the screen is arranged between the upper side and the transponder. In particular, the screen opening faces the upper side and/or the transponder. In particular, the screen is arranged such that a plane of the screen opening is parallel to the upper side and/or perpendicular to a connecting line between the transponder and the upper side. In other words, the screen opening preferably has a maximum screen opening surface when viewed from an upper side of the transponder installation module toward the transponder.

The transponder installation module, which is built into or inserted into the prepared depression or opening, thus improves signal-technical communication between the transponder on the one hand and an external reading and writing device that is arranged or arrangeable on the other hand. Since the structural immediate environment of the transponder is essentially predetermined by the transponder installation module, which has an essential effect on the transmission, no adaptation of the medical instrument is required with regard to reception of the transponder.

In other words, the transponder installation module is based on the underlying idea that if in particular a signal-permeable housing is selected (comprising e.g. thermoplastic, duroplast, plastics in general, and/or silicone as material), the reading and/or writing distance is optimized by a metal screen/reflector/screen with screen opening which is at least partially surrounding the housing and thus the transponder, which distances the transponder from the upper side and thus from a reading and writing device that can be arranged there, with a geometrically defined opening.

The transponder installation module can be integrated even better and more flexibly into the medical instrument. The medical instrument requires only one, in particular standardized, prefabricated/prepared depression or opening or sink or cavity on or respectively in the instrument body surface. In other words, the lower side as well as the transponder are arranged further/deeper in the direction of the depression than the screen and the upper side of the transponder installation module. In particular, the design of the transponder installation module allows it to be insertable completely in an underfloor manner, so that the upper side is flush with the instrument body surface or is set back relative to it in the direction of the instrument body interior.

With the aid of the transponder installation module, for example, a product-related reprocessing cycle with corresponding information can be recorded, documented and the knowledge gained from this can be further processed. Such a reprocessing cycle may include, for example, cleaning and/or sterilization and/or oiling. With the aid of the transponder installation module, so-called tracking as well as lifecycle management of a medical device/of a medical product, in particular a medical instrument, can be carried out. The information also serves the manufacturer with regard to evidence in the event of a complaint. Furthermore, a user can subject a medical device, in particular a medical instrument, equipped with the transponder installation module to maintenance only when there is an individual need to carry out maintenance, and no longer has to follow a predefined maintenance interval. This benefits the availability and provision of medical instruments, since maintenance intervals can be extended individually.

In other words, the transponder installation module according to the invention can be used to document information in the medical instrument itself. This has the advantage of transparency in the case of service (transponder, in particular glass tag or RFID chip of the glass tag, carries the information), determination of a running time, tracking in business models such as the so-called pay per use, indication of a service life (MDR requirements, standard requirements), wherein receivability of the transponder of the transponder installation module, when it is inserted into the medical instrument, is improved.

The mounted state or assembled state is defined as the state of the transponder installation module in which all its components are fully mounted or assembled and the transponder installation module is available as a finished unit or assembly and is installable or insertable in the medical instrument.

The installed or inserted state, on the other hand, refers to the state in which the transponder installation module (in the assembled state) is installed or inserted in a medical device, in particular in a medical instrument, more specifically in the prepared depression or opening.

In particular, the transponder installation module and, in particular, the housing may be provided and configured to be assembled and/or disassembled or respectively inserted and/or removed without tools into the prepared depression or opening of the medical instrument. Further preferably, the housing of the transponder installation module may be provided and adapted to form a press fit in the prepared depression or opening. In particular, a side wall of the housing, or at least a section of the side wall, arranged between the upper side and the lower side can be configured in such a way that it causes bracing or an elastic pretensioning force transverse to a connecting line between the upper side and the lower side and/or parallel to the instrument body surface in order to hold the transponder installation module in its inserted state or in position via a force fit, in particular a frictional fit. This allows a particularly simple, reversible mounting or insertion into the medical instrument. Replacement of the entire assembly of the transponder installation module is also particularly quick and easy. In addition, the medical instrument is not damaged during replacement. The replacement can also be carried out particularly quickly.

Preferably, the transponder installation module may be provided and configured for being assembled or respectively mounted without tools. The components or parts of the transponder installation module may be assembled to form the insertable assembly in particular via at least one plug-in and/or clip connection. This further simplifies assembly and disassembly.

Preferably, the screen may be configured in several parts, in particular in two parts, and may be provided and adapted to fix the housing, which is also configured in several parts, in particular in two parts, and thus to secure it against each other. The screen thus fulfills two main functions. On the one hand, in the assembled state, it improves the reception of the transponder in terms of signal technology via its screen opening and, at the same time, it provides a mechanical, form-fitting fixing and securing of the multi-part housing.

Preferably, the screen may be configured in several parts and may comprise a first screen segment and a second screen segment, which are capable of being brought into latching engagement and/or out of latching engagement with each other in a form-fitting manner via a latching mechanism. The term latching engagement in this context refers to a form-fitting operative engagement of the latching mechanism in which a movement of the first screen segment relative to the second screen segment against a direction in which they were assembled is prevented or at least strongly inhibited.

According to an embodiment, the first screen segment and the second screen segment can prevent insertion and removal of the transponder from the housing in the form-fitting latching engagement. The mechanical latching of the latching mechanism ensures that the transponder, in particular the glass tag, is held securely in position in the housing, in particular between two housing parts of the housing.

In particular, the screen is configured to be flat or sheet-like, especially flat/planar, and has a constant height (thickness) perpendicular to the screen opening, similar to an elongated ring washer. In the case of a curved screen, in particular with a constant bending radius, which preferably corresponds to a radius of an instrument body surface, the screen may also have a constant thickness.

Further preferably, the first screen segment and the second screen segment may be the same/identical components. In particular, the screen opening may have an elongated or slotted shape with a longitudinal axis of the screen opening. Preferably, both screen segments may have a U-shaped configuration, wherein a respective latch projection extending orthogonally to the longitudinal axis of the screen opening is configured at a first free end, and a complementary latch depression extending orthogonally to the longitudinal axis of the screen opening is configured at a second free end. In particular, the latch projection and the latch depression point in the same direction so that when the first screen segment is rotated by 180° about the longitudinal axis of the screen opening relative to the second screen segment, the two identical screen segments can be brought into latching engagement with each other at both free ends. The latch projection then engages the latch depression. In particular, the latch projection points outward and away as seen from the screen opening, and the latch depression points toward the screen opening. Further preferably, the latch projection is configured in the form of a, in particular symmetrical, convex hill, similar to a P-shape, and the latch depression is configured in the form of a complementary, in particular symmetrical, concave sink. In particular, the U-shaped screen segments have a circumferential, rectangular cross-section with constant dimensions, wherein the dimension (width) is reduced only in the area of the free ends at the latch projection and the latch depression orthogonal to the longitudinal axis of the screen opening, so that the width of the latch projection and the latch depression are smaller. In particular, the latch projection is set back from an outer side of the screen segment facing away from the screen opening and/or the latch depression is set back from an inner side of the screen segment facing toward the screen opening.

According to a further preferred embodiment of the invention, the screen may comprise metal as a material, in particular it may be made entirely of metal. Preferably, the screen is made of stainless steel. Metal is impermeable to electromagnetic waves. Stainless steel can be sterilized particularly well.

Further preferably, the screen opening serving as a passage for electromagnetic waves or signals, in particular radio signals, is configured to be elongated or slot-shaped and has a (slot) width corresponding to the product of coil diameter (of the transponder, in particular of the glass tag) and an ideal factor, wherein the ideal factor is in the range of 1.3 to 2.2, more preferably in a range of 1.6 to 1.9, and most preferably 1.75. In other words, the screen opening that is parallel to the transponder, in particular the glass tag, has a width that is greater than the coil diameter and/or a width of the transponder, in particular a diameter of the glass tag.

Further preferably, the elongated or slot-shaped screen opening has a length which is −30% up to +50% of the total length of a coil core, in particular a ferrite core, of the transponder, more preferably a length of 0% up to +30% of the total length of the ferrite core, and particularly preferably a length of +15% of the total length of the ferrite core. In other words, the screen opening that is parallel to the transponder, in particular the glass tag, has a length that is preferably greater than the length of the coil core, in particular of the ferrite core, and/or of the transponder, in particular glass tag.

In particular, the housing may comprise a first housing part and a second housing part, between which the transponder is received in a fixed position, wherein the screen fixes the first housing part to the second housing part.

Preferably, the housing may comprise exactly two housing parts and the screen may comprise exactly two screen segments. This minimizes a number of components and facilitates assembly.

According to a further preferred embodiment, the second housing part may be U shaped with a semicircular/semi-cylindrical housing base and two adjoining parallel cylindrical housing pins/holding arms, which in particular have rounded heads that can be inserted into two parallel, complementary receptacles/counter-openings formed in the first housing part in the manner of a form-fitting plug-in connection, wherein the screen form-fittingly engages around the two housing parts in the assembled state and fixes them against each other. Preferably, the second housing part has a stepped shape with at least two different diameters in its semi-cylindrical housing base as viewed from the lower side to the upper side. This creates a kind of stepped, longitudinally cut corrugation, wherein the screen or the screen segment can be inserted into the step with the smaller diameter in such a way that the screen rests against the housing base and, in particular, with the same diameter of the housing base (with the larger diameter) and a partial area of an outer wall of the screen, both end flush with each other. Alternatively, the screen may be slightly recessed from the outer side of the housing base in the direction of the housing interior so that, when inserted, it does not come into contact with an inner wall of the prepared depression or opening and only the housing rests in the depression or opening.

Preferably, only the two cylindrical pins configure those outer surfaces of the housing which project outward toward the sides of the housing, abut the inner wall of the prepared depression or opening and, in particular via their inherent elasticity, effect bracing or a press fit in the depression or opening.

Preferably, a circumferential groove is configured in the housing in the area of the upper side, which is open toward the outer side of the housing and into which the screen can be inserted. In particular, the screen inserted into the circumferential groove is flush with the outer side of the housing or is set back from it into the housing interior.

Furthermore, the housing may preferably be made of thermoplastic material, in particular polypropylene (PP), and particularly preferably may be made entirely of this material. Thermoplastic is permeable to electromagnetic waves and is cheap and easy to manufacture.

Preferably, the housing of the transponder installation module, in particular the upper side, may have a color or be color-coded so that information is assigned to the transponder installation module by way of color coding. In particular, an instrument system with a matching set of medical instrument and compatible transponder installation module can be created. Preferably, in this case, only a first transponder installation module, which is marked with a first color, can be inserted into a first medical instrument with a first prepared depression or opening, and a second medical instrument can receive only a second transponder installation module, which is characterized with a second, different color. This can ensure, for example, that only the first transponder installation module is used for the first medical instrument, which is individually adapted to it, whereas only the second transponder installation module is used for the second medical instrument, which is individually adapted precisely to it. Different colors may thus be used for structure management and identification. Alternatively or in addition to the colors, a corresponding different, set-wise geometry of the depression or opening and of the housing can be selected, so that accidental interchanging is prevented.

In particular, the housing has a flat upper side and a flat lower side as well as a circumferential, in particular closed, side surface arranged between the upper and lower sides, so that the position-fixed transponder is circumferentially delimited from the environment.

In particular, the upper side may be configured with a flat surface and a plane of the screen opening parallel to the upper side. Preferably, the lower side may also be configured with a flat surface and a plane of the screen opening parallel to the lower side. In particular, the flat planes of the upper side, lower side, and screen opening are parallel to each other.

Preferably, the first housing part forms the upper side. Further preferably, the first housing part also forms more than half of the lower side. Thus, the second housing half primarily serves to seal the held transponder and preferably to provide a press fit, whereas the first housing part in the inserted state provides mechanical shielding through the upper side.

Preferably, the housing may have rounded or cut edges on its lower side. This improves centering and insertion in the prepared depression or opening with the lower side first.

Preferably, the first housing part may be connectable to the second housing part via a plug-in connection and, further preferably, the plug-in connection may be secured against unintentional falling out via a press fit.

According to an embodiment of the invention, a cylindrical recess/borehole, into which a cylindrical transponder is insertable, may be provided in the housing, in particular in the first housing part. Preferably, the diameter of the recess is adapted with respect to the geometry of the transponder to form a press fit. In particular, the diameter of the recess corresponds exactly to the diameter of the cylindrical transponder. Alternatively preferably, the diameter may be slightly smaller than the diameter of the transponder to form a friction-fit press fit. Preferably, this recess is parallel to and symmetrically located between the housing pins in the assembled state. Preferably, the recess is parallel and symmetrically located between two channel-shaped receptacles of the first housing part open toward the respective outer side of the housing. In other words, the housing, in particular the first housing part, may have three parallel bores wherein one of them is arranged between two other bores and is a cylindrical bore in the solid material and the other two bores are only half bores which are open to respective outer sides facing away.

According to a further embodiment of the invention, the housing and/or the screen may be provided with a biocide so that the risk of germ formation is further reduced.

According to an embodiment of the invention, the housing, in particular the first housing part, may have a flat, rectangular, in particular planar thin cover as the upper preferably having rounded corners, which, when viewed on the upper side, covers the entire housing and thus represents a type of protective cover for the transponder installation module. In particular, the cover is designed with tabs all around its sides, so that the transponder installation module can be easily removed manually. In particular, a circumferential groove open toward the outer side may be configured in the first housing part in a plane parallel to the cover between the cover and the lower side, in particular directly under the cover, in which the cover can be inserted.

According to an embodiment of the invention, the transponder may have a cylindrical shape, in particular with rounded ends, with a longitudinal axis of the transponder, and the screen opening of the screen may be configured to be elongated or slot-shaped and may have a longitudinal axis of the screen opening, wherein the longitudinal axis of the transponder is arranged parallel to and spaced from the longitudinal axis of the screen opening. In particular, the screen opening faces the upper side.

According to a further preferred embodiment, the upper side and the lower side may be configured to be flat and parallel to each other, wherein the longitudinal axis of the transponder and the longitudinal axis of the screen opening lie in a plane of symmetry of the housing, which intersects the upper side and the lower side perpendicularly.

Preferably, the transponder is arranged centrally and symmetrically with respect to the screen opening as seen from the upper side in the direction of the lower side. This means that the transponder is centered in the screen opening and reception is improved.

Preferably, the transponder may be a passive RFID transponder.

Preferably, the transponder is an RFID transponder, especially preferably a glass tag, for storing information associated with a particular medical instrument. This RFID transponder is adapted to be individualized according to the requirements of a predefinable process. In particular, the RFID transponder or RFID tag has:
  a microchip, preferably with a dimension of less than 2 millimeters,
  an antenna, preferably in the form of a coil, particularly preferably with an internal, rod-shaped ferrite core around which the coil is wound, and
  a sheathing, wherein the sheathing is preferably waterproof and/or airtight and preferably protects the electronics of the transponder from the environment.

According to a further embodiment, the transponder may also be an active RFID transponder comprising at least one energy source, preferably in the form of a battery, accumulator and/or capacitor.

Preferably, the transponder is provided and adapted to store at least one of the following information in encrypted or unencrypted form:
  general condition,
  service life/end of service life,
  maintenance interval,
  performance and suitability for follow-up operation,
  low maintenance of product and product damage, if any,
  temperature overshoot and undershoot and product damage, if any,
  part number,
  serial number, and/or
  customer.

This makes it possible to record and count processing cycles for medical instruments, in particular in combination with individualized storage, and to save this information in the medical instrument itself. In particular, it is possible to determine whether all the necessary process steps have been observed and carried out. A number of processing cycles may, in particular, be a proportional measure to the above information.

Preferably, the transponder has a cylindrical shape with rounded ends. In particular, the shape of the transponder, in particular the glass tag, is a pill shape.

According to a preferred embodiment, the size of a glass tag may be 2 mm in diameter and 12 mm in length. Alternatively, the dimension may preferably be 3 mm in diameter and 13 mm in length or preferably 4 mm in diameter and 22 mm in length.

In addition, the transponder may preferably use a frequency band in the range of 12 to 15 MHz, advantageously in the range of 13 to 14 MHz, more preferably in the range of 13.4 to 13.7 MHz, and particularly preferably of 13.56 MHz.

Preferably, the medical instrument may be a surgical instrument, a monopolar HF instrument, a bipolar HF instrument, an electrosurgical instrument, an ultrasound instrument, a surgical clip, a surgical clamp, surgical forceps, surgical scissors, or a scalpel. In particular, the medical instrument may be a handpiece with an integrated motor and/or a tool that is engageable by coupling with the handpiece.

Preferably, the transponder installation module is provided and configured for underfloor/undersurface insertion into the medical instrument so that it does not protrude above the surface.

In particular, the medical instrument has an elongated hole as a prepared opening in its surface into which the transponder installation module is inserted.

According to an embodiment, the medical instrument may have a feather key groove or a longitudinal groove with, in particular, rounded corners and/or ends in its instrument body surface as a prepared depression.

In principle, the geometry and the material of the medical instrument and/or of the housing of the transponder installation module as well as the orienting of the transponder with respect to the corresponding instrument body surface are freely selectable and depend mainly on the design of the transponder installation module. However, an orientation, in particular of the coil, of an elongated transponder is preferred such that the transponder is oriented in its longitudinal direction in the inserted state parallel to the external surface of the body of the medical instrument (i.e. 'lying'). In particular, the housing may optionally remain free/open to the outside or may be filled/closed with a signal-permeable material. In particular, the transponder may already be shaped per se in the manner of a sealing cap in such a way that, when the transponder is inserted into the housing (through the screen opening), the housing or its opening is sealed (waterproof/airproof) to the outside by the transponder itself.

The object of the present invention is solved with respect to a medical transponder system/transponder communication system according to the invention in that it comprises a transponder installation module or a medical instrument according to the invention with a transponder installation module and a reading and/or writing device which is signal-technically coupleable to the transponder, which is in particular configured with an instrument holder or is itself an instrument holder, which is adapted to hold or temporarily fix the transponder installation module or respectively the medical instrument with the transponder installation module in a predetermined position and/or orientation relative to the reading and/or writing device, in which a signal transmission between the transponder and the reading and/or writing device is enabled. In other words, the medical instrument or the medical device can be read and/or written to by a reading and/or writing device that can be brought into close proximity, in particular a distance of less than one centimeter, to the transponder. In the case of medical instruments that have a connection, for example for an air supply, a power supply and/or a data exchange, this read-out device can be attached to the medical device in the couplable adapter for the counterpart.

BRIEF DESCRIPTION OF THE DRAWINGS

The invention is explained in more detail below with the aid of preferred embodiments with reference to accompanying figures. The following is shown:

FIG. 12 shows a top view of a medical instrument according to the invention with the inserted transponder installation module of FIGS. 1 to 10;

FIG. 13 shows a top view of the medical instrument of FIG. 12 which is coupled to a handpiece;

FIG. 14 shows a perspective view of a medical instrument of a further preferred embodiment in the form of a medical punch with transponder installation module;

FIG. 15 shows a perspective view of a medical instrument of a further preferred embodiment in the form of medical scissors;

FIG. 16 shows a top view of a medical instrument of a further preferred embodiment in the form of a punch;

The figures are merely schematic in nature and are intended only to aid understanding of the invention. Identical elements are provided with the same reference signs. The features of the various configuration examples can be interchanged.

DETAILED DESCRIPTION

Figure 1:
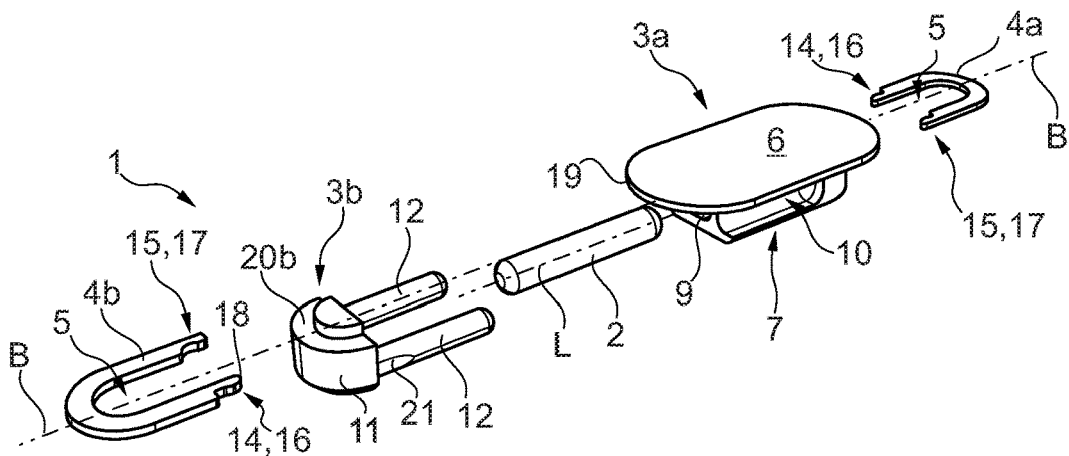
FIG. 1 shows a perspective view of an upper side of a transponder installation module of a medical instrument according to the invention of a preferred embodiment in exploded view.
Figure 2:
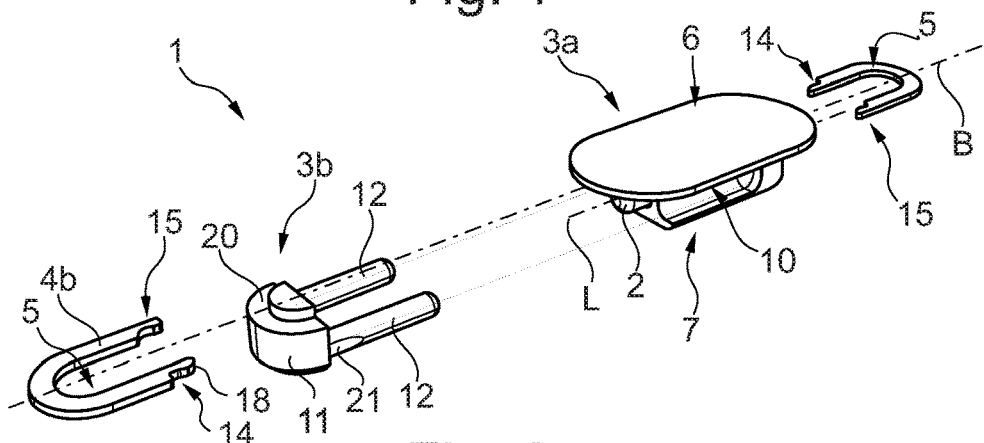
FIG. 2 shows a perspective view of the transponder installation module of FIG. 1, in which a transponder is inserted into a housing part.
Figure 3:
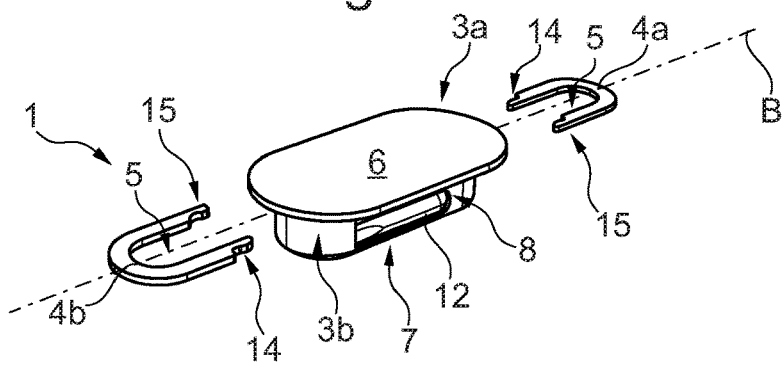
FIG. 3 shows a perspective view of the transponder installation module from FIGS. 1 and 2, in which the housing parts are assembled.
Figure 4:
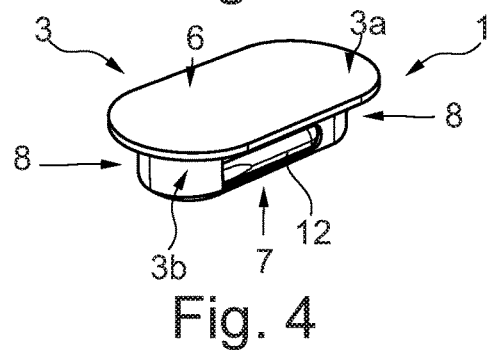
FIG. 4 shows a perspective view of the transponder installation module from FIGS. 1 to 3, in which the two-part screen has been assembled.

FIGS. 1 to 10 show a transponder installation module 1 of a medical instrument 101 according to the invention (see FIG. 12) of a preferred embodiment, which is provided and adapted to be inserted into a prepared depression 103 in an instrument body surface 104 of the medical instrument 101. In this regard, FIG. 1 is a perspective view of an exploded view of the transponder installation module 1 showing the individual components of the transponder installation module 1 prior to assembly. FIGS. 2 to 4, which follow FIG. 1, show a step-by-step tool-free assembly of the individual components up to the fully mounted transponder installation module 1 shown in FIG. 4 in the assembled state. FIGS. 5 to 8 show the transponder installation module 1 of FIGS. 1 to 4 from a bottom view.

Specifically, the transponder installation module 1 has a single pin-shaped or pill-shaped transponder in the form of a glass tag 2 with a longitudinal axis L, whose sheathing is configured rotationally symmetrically from glass. In the present embodiment, the glass tag 2 is an embeddable RFID (Radio Frequency Identification) glass tag with preferably a frequency of 13.56 MHz.

The glass tag 2 is held fixed in position via a housing 3 made of thermoplastic, preferably polypropylene. A thermoplastic, and in particular polypropylene, is a low-cost material suitable for injection molding, but which is signal-permeable for electromagnetic signals, in particular for the radio frequency (RF) range. Thus, the housing 3 provides a good structural holder for the glass tag 2 without affecting it in terms of signaling. As described in detail below, the housing 3 is further configured to be inserted into the prepared depression 103 or respectively sink of the medical instrument 101 (see FIG. 12).

In addition to the signal-permeable housing 3, the transponder installation module 1 has, in accordance with the invention, a screen or reinforcing screen 4, in particular consisting of several parts, made of an electromagnetically signal-impermeable or conductive material, in this embodiment metal. In the assembled or respectively mounted state, this screen 4 has a screen opening 5 which is offset with respect to the transponder 2 toward an upper side 6 of the transponder installation module 1 and, due to its special geometric configuration and position, has the effect that reception of the glass tag 2 is significantly improved. In particular, the screen 4 increases the possible distance to a reading and writing device that can read, modify and/or write to the transponder.

Thus, by this particular embodiment of the transponder installation module 1, the screen 4 is arranged between the transponder 2 and an external reading and writing device positionable in the area of the upper side 6 of the transponder installation module 1, wherein the screen opening 5 faces both the transponder 2 and the upper side 6. This arrangement applies equally to the state when it is inserted in the medical instrument 101.

By increasing the technical signal-related distance or increasing the maximum possible technical signaling distance, on the one hand reception of the transponder in the form of the glass tag 2 is improved and thus in particular reliable, stable and secure communication is made possible, and on the other hand independent or at least even more independent development of the medical instrument is realized. In fact, since the structural immediate environment of the transponder is mainly determined by the transponder installation module 1, which essentially determines the transmission, there is no need for further adaptation of a medical instrument with regard to reception of the transponder.

The transponder installation module 1 can be integrated even better and more flexibly into the medical instrument 101 (see FIG. 12). The medical instrument 101 requires only a prepared depression or opening on or respectively in an instrument body surface matching the housing 3, into which the transponder installation module 1 is inserted with its lower side 7 pointing in the direction of the depression, so that the lower side 7 is set back relative to the upper side 6 of the transponder installation module 1 and thus relative to an instrument body surface 104. In particular, the design of the transponder installation module 1 allows it to be used in an underfloor manner so that the upper side 6 is flush with the instrument body surface 104 or is set back from it in the direction of the instrument body interior.

In this embodiment, the upper side 6 and the lower side 7 of the housing 3 are both planar surfaces that are parallel to each other and that delimit the transponder installation module 1 to an upper side and to a lower side from an environment (material).

Figure 8:
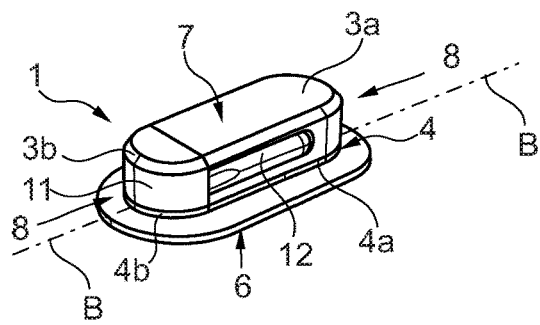

More precisely, the housing 3 in the assembled state, see FIG. 4 and FIG. 8, has substantially three main sides, i.e. firstly the plane, flat, rectangular lower side 7 with rounded corners, secondly the plane, flat, rectangular upper side 6 with rounded corners, which is parallel to the lower side 7 and larger in area than the lower side 7, and thirdly a circumferential outer side/circumferential wall 8, which is arranged between the lower side 7 and upper side 6 and encloses the transponder. The outer side 8 follows the outer contour of the lower side 7 and extends perpendicularly to it and perpendicularly to the upper side 6, forming a kind of wall. As a result, the transponder installation module 1 is sealed off (planarly) from its surroundings when assembled.

In addition to insertion, replacement of the transponder installation module 1 is also particularly simple. This is because the transponder installation module 1 does not have to be fastened to the medical instrument via welding or screws, for example, and then be removed again in a correspondingly time-consuming manner; instead, it can simply be inserted into the prepared depression 103 of the medical instrument 101 (see FIG. 12) and can be removed from it again without the need for tools. By using a thermoplastic as material as well as the geometric design of the housing 3, which will be described in more detail below, the housing 3 has a certain inherent elasticity in a direction parallel to the upper side 6 in order to effect a press fit or a force fit, respectively, in the inserted state. Since the structural conditions or parameters substantial for the transmission are already realized in the transponder installation module 1 itself, the medical instrument may optionally have a signal-permeable as well as a signal-impermeable core.

In the assembled state, the screen 4 has a planar, elongated O shape with a constant wall thickness both in a plane of the screen 4 and orthogonal to it. This uniform frame of the screen 4 results in a central, elongated or slot-shaped screen opening 5, which is also configured to be O shaped and axis-symmetrical and has a longitudinal axis B of the screen opening. In this embodiment, the longitudinal axis B of the screen opening is simultaneously a longitudinal axis of the screen 4 due to the symmetrical configuration.

Specifically, the longitudinal axis L of the glass tag is parallel to the longitudinal axis B of the screen opening, wherein the longitudinal axis L of the glass tag is set back from the longitudinal axis B of the screen opening toward its lower side 7. The longitudinal axis L of the glass tag and the longitudinal axis B of the screen opening define a plane which represents a symmetry plane for the housing 3 of the transponder installation module 1.

The glass tag 2 is particularly small, so that a small dimension of the transponder installation module 1 can be realized in combination with a small housing 3.

A special feature of the transponder installation module 1 of the present invention is the multi-part, in this embodiment two-part, configuration of the screen 4. Due to this two-part embodiment of the screen 4, in interaction with the multi-part, in this embodiment two-part, housing 3, a structural fixation of the two-part housing 3 can be achieved in addition to a signal amplification, as explained below.

In particular, the two-part housing 3 has a first housing part 3a and a second housing part 3b different from the first. The integrally configured first housing part 3a has an axis-symmetrical and mirror-symmetrical configuration and configures the flat upper side 6 and a main part of the flat lower side 7. Centered between the upper side 6 and lower side 7 and in the plane of mirror symmetry, the first housing part 3a has a pill-shaped or cylindrical recess/drill hole 9, which corresponds to the dimensions of the glass tag 2, so that it can be inserted into the recess 9. Preferably, the dimension of the recess 9 can be selected relative to the dimension of the glass tag 2 so that there is a press fit. In this way, the glass tag 2 is secured against unintentional falling out and can only be removed again via a tensile force in the direction of its longitudinal axis L. Alternatively, a radial clearance may be provided between the sectionally circular recess 9 and the sectionally circular glass tag 2 so that it is particularly easy to insert and remove. In other words, a diameter of the recess may be slightly less than or equal to a diameter of the glass tag 2 so that a press fit is provided, or the diameter of the recess 9 may be made slightly larger so that the glass tag is easily insertable and removable with clearance.

At the same height between the upper side 6 and lower side 7 as the recess 9 and parallel thereto, the first housing part 3a has a semicircular channel/trough 10 symmetrically offset toward its sides and open toward the outside. The two channels 10 are again configured to be mirror-symmetrical with respect to the inserted glass tag 2 with longitudinal axis L and serve to accommodate a second housing part 3b.

Like the first housing part 3a, the second housing part 3b is configured to be mirror-symmetrical. It is U shaped with a semicircular or semi-cylindrical housing base 11 and two parallel cylindrical housing pins/pins 12 adjoining the housing base 11. The housing pins 12 with rounded heads for improved insertion are provided and configured to engage in the channels 10 and to serve as a plug-in connection. The diameter of the housing pins 12 corresponds to the diameter of the channels 10. As with the recess 9, a press fit or a fit with clearance can be set by matching the diameter of the housing pin 12 to the diameter of the channel 10. Likewise, by matching the distance between the longitudinal axes of the housing pins to a slightly smaller distance than the distance between the longitudinal axes of the channels, a contact force with accompanying friction can be achieved between the housing pins 12 and the channels 10, so that the second housing part 3b is fixed in a force-fit manner to the first housing part 3a and is secured against unintentional separation. The second housing part 3b can only be pulled out from the first housing part 3a by applying a tensile force parallel to the longitudinal axes of the pins.

Figure 5:
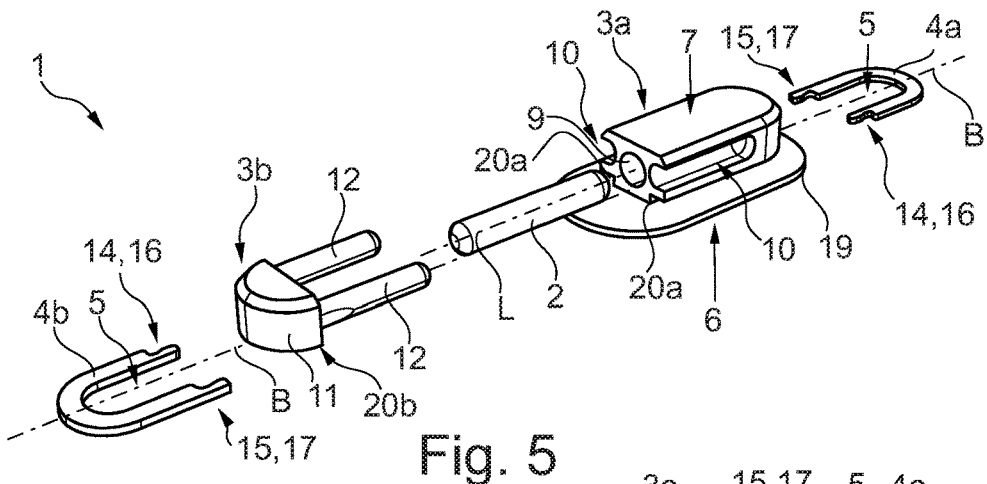
FIGS. 5 to 8 show a corresponding perspective view of a lower side of the transponder installation module of FIGS. 1 to 4.
Figure 6:
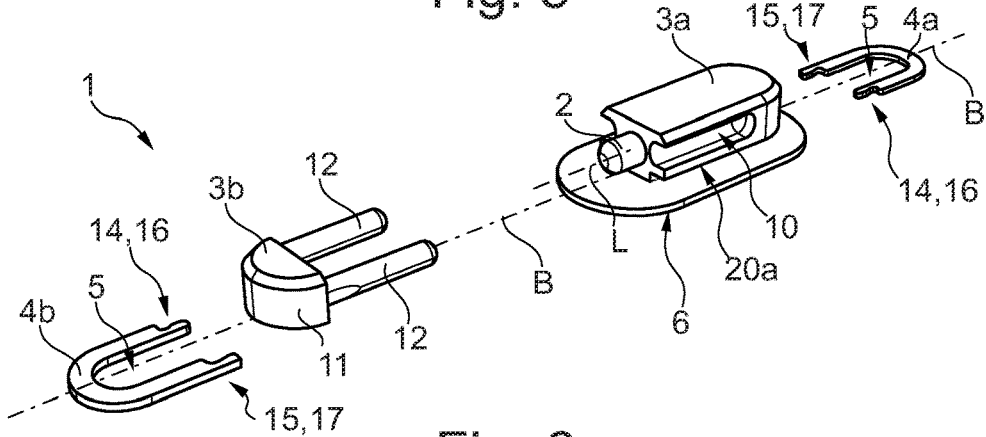
Figure 7:
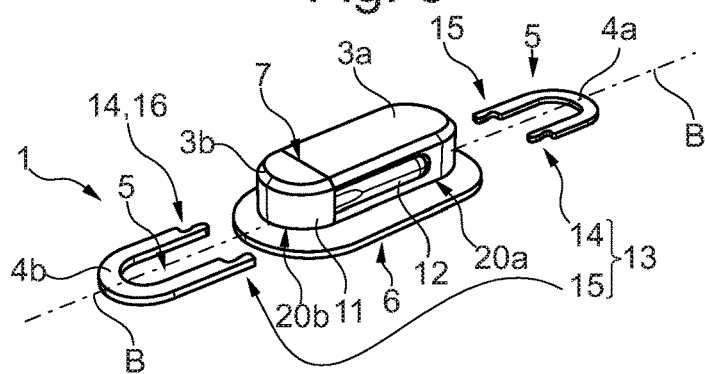

For assembly, the second housing part 3b is moved translationally in the direction of the longitudinal axis L of the glass tag 2, as shown in FIGS. 2 and 3 or respectively FIGS. 5 and 6. The housing pins 12 subsequently engage the channels 10, and finally the housing base 11 abuts the first housing part 3a. The two housing parts 3a, 3b can only be moved in one direction along the longitudinal axis L.

In the assembled state of the housing 3, see FIGS. 3, 7 or FIGS. 4, 8, respectively, the two housing parts 3a, 3b enclose the glass tag 2 between them, protecting or delimiting it from the environment.

In order to prevent the two housing parts 3a, 3b from detaching from each other unintentionally, they are secured or respectively fixed against each other in a form-fit manner without tools by the two-part screen 4. In this embodiment, the two-part screen 4 has a first U-shaped screen segment 4a and a second U-shaped screen segment 4b, which surround the outer circumference of the two housing parts 3a, 3b (see FIGS. 4 and 8) and which can be connected to each other via a form-fit latching mechanism/clip system 13. In the assembled state, in which the two screen segments 4a, 4b are then latched and connected to each other, movement of the two housing parts 3a, 3b apart in the direction of the longitudinal axis L of the glass tag 2 is then prevented, since the two-part screen 4 surrounds both the first housing part 3a and the second housing part 3b around their outer circumference and holds them together like a rigid rope. The screen 4 thus has both the function of signal amplification of the transponder and the function of a fixing element that holds the housing 3 together.

Both screen segments 4a, 4b are identical components in which the second screen segment 4b has been rotated by only 180° around the longitudinal axis B of the screen opening compared to the first screen segment 4a. Therefore, only the structure of the first screen segment 4a is described below.

The first screen segment 4a made of metal, in particular stainless steel, has a profile that is rectangular in section and runs in a U shape. The screen segment 4a as a whole is configured planar or lies in one plane, respectively. Furthermore, the first screen segment 4a has, at a first free end 16, a latch projection 14 extending orthogonally to the longitudinal axis B of the screen opening and lying in the aforementioned plane, in the form of a convex hill facing away from a second free end 17. In addition, the screen segment has at the second free end 17 a complementary latch depression 15 extending orthogonally to the longitudinal axis B of the screen opening in the form of a cavity complementary to the hill and facing the first free end 16. Here, latch projection 14 and latch depression 15 point in the same direction.

Figure 9:
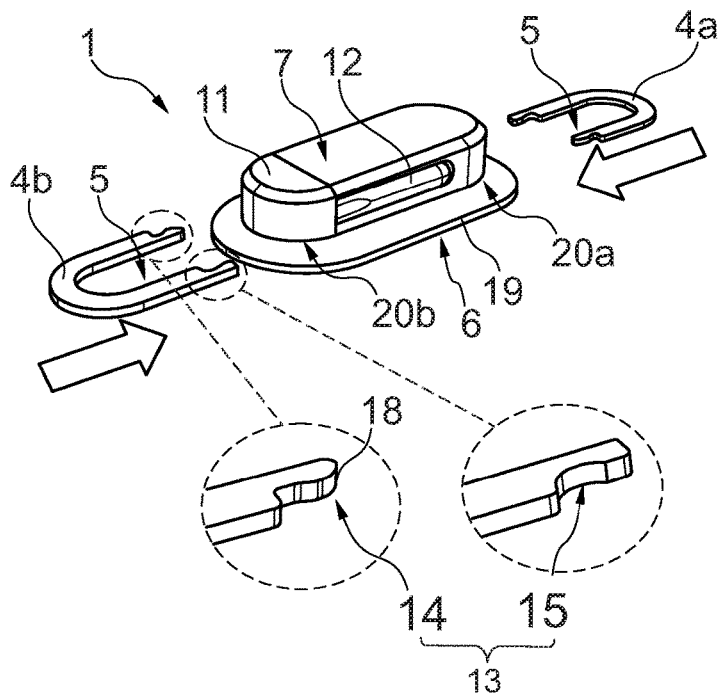
FIG. 9 shows a view analogous to FIG. 7 with two detailed views of the free ends of a screen segment and indicated direction of force and movement during assembly of the screen.

The latching effect is as follows and is shown in FIG. 9. The first free end 16 of the first screen segment 4a is brought to the second free end 17 of the second screen segment 4b. Thereby, the latch depression 15 of the first screen segment 4a initially rests against a running surface 18 in the area of the complementary latch projection 14 of the second screen segment 4b. If the two screen segments 4a, 4b are now pushed further toward each other, the geometry of the latch depression 15, which abuts the running surface 18, causes the second free end 17 to be elastically deflected outward substantially orthogonally to the longitudinal axis B of the screen opening against an internal stress of the screen segment 4a, so that the latch depression 15 then lies above the running surface 18 and the first free end 16 is displaceable relative to the second free end 17. This process occurs analogously at the second free end 17 of the first screen segment 4a together with the first free end 16 of the second screen segment 4b.

If the two screen segments are now moved further toward each other, the respective latch recess 15 finally engages in the latch projection 14 and the second free ends 17 are deflected back in the direction of the pretension. The first screen segment 4a is in form-fit latching engagement with the second screen segment 4b and fixes the first housing part 3a to the second housing part 3b. The latch projection 14 and the latch recess 15 together with the U shape of the screen segment 4a, which ensures a certain elasticity, thus form the latching mechanism 13.

By adapting the shape of the latch projection and of the complementary latch depression, a required deflection force can be set in particular. For example, a latch tooth shape may be used instead of a hill shape. This makes it possible to prevent or at least make it more difficult to disassemble the transponder installation module during latching.

The housing 3 has a circumferential groove 20 along its outer side 8 so that the screen 4 can fully enclose the housing 3. Specifically, the first housing part 3a has a U-shaped, circumferential first groove 20a, into which the first screen segment 4a and a section of the second screen segment can be inserted, and the second housing part 3b has a U-shaped second groove 20b at its housing base 11, which is adapted to the second screen segment 4b and into which the second screen segment 4b is insertable in a form-fit manner.

It should be noted at this point that both screen segments 4a, 4b may of course also be rotated by 180° around the longitudinal axis of the screen opening and continue to perform the same function.

A planar, thin cover 19 with rounded corners forms the upper side 6 and protects the transponder installation module 1 from the environment in the inserted state. A transition 21 on the sides of the housing pins 12 facing outward defines a reduction of a maximum distance between outer surfaces of the housing pins 12 toward the housing base, so that there the diameter of the housing base 11 is equal to the distance. As a result, only the section of the housing pins 12 without transition 21 is used for the press fit, since the distance between the opposing surfaces is (slightly) greater there.

Figure 10:
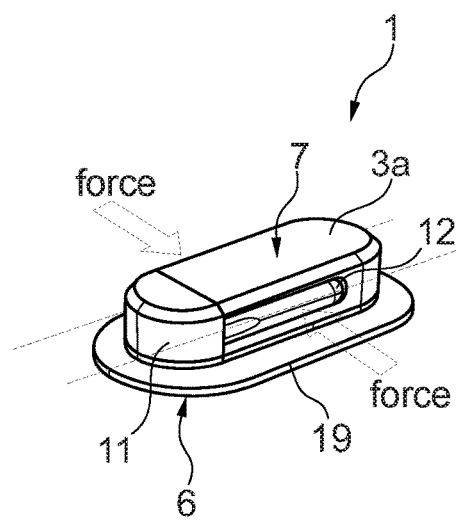
FIG. 10 shows a view analogous to FIG. 8 with pressing force on two housing pins, which occur in the inserted state and hold the transponder installation module in a force-fit in the medical instrument.

FIG. 10 shows a contact force of the depression 103 occurring in the inserted state on the two housing pins 12, which have the greatest width of housing 3, protrude in a manner of speaking, and accordingly abut against respective inner sides of the depression 103.

Figure 11:
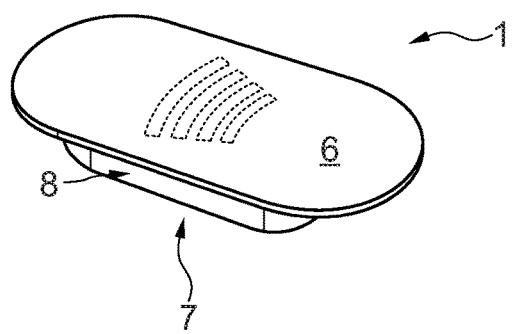
FIG. 11 shows a perspective view of a transponder installation module of a further embodiment with color coding.

FIG. 11 shows a further embodiment of a transponder installation module 1. In this embodiment, the transponder installation module 1 has color coding in the form of a green surface on its upper side 6. The color coding allows several functions to be implemented. For example, when a transponder installation module 1 is replaced, a new color can be used so that it is visually visible to a user which instrument has already been equipped with a new transponder installation module. Alternatively or additionally, it may be provided that certain colors only match certain medical instruments, similar to a size or identification indication. It is also possible, for example, to indicate the date of manufacture or replacement of a transponder installation module 1 in color, similar to vehicle stickers.

FIG. 12 shows a medical instrument 101 according to the invention of a preferred embodiment with the transponder installation module 1 inserted. In this case, the transponder installation module 1 is inserted into the matching, prepared depression 103 of a sleeve-shaped coupling portion 102 at a distal region of the medical instrument 101. Specifically, the depression 103 is configured in the form of an elongated groove having rounded ends and the same depth relative to an instrument body surface 104. The housing 3 and the depression 103 are matched to each other such that the transponder installation module 1 has a press fit in the medical instrument 101, so that the transponder installation module 1 can be inserted and removed without tools. The upper side 6 of the transponder installation module 1 is flush with the instrument body surface 104, so that a quasi planar instrument body surface without undercuts or projections is provided. In particular, the depression 103 may be configured in a step-like manner when viewed in a depression direction V (not shown here).

In an alternative embodiment, the upper side of a transponder installation module may also be convex to better match or respectively fit a cylinder shape.

FIG. 13 shows the medical instrument 101 from FIG. 12 coupled to a handpiece 105. A metallic sleeve portion 106 of the handpiece 105 covers the transponder installation module 1 so that to it is protected from the environment both mechanically and in terms of signaling, and reading out when coupled to the handpiece 105 is prevented. In addition, the transponder installation module 1 is secured against falling out.

Figure 17:
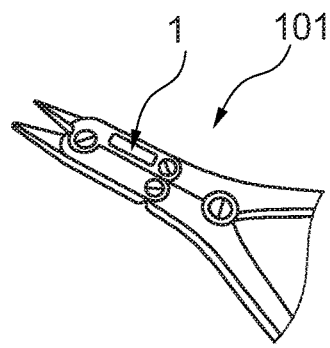
FIG. 17 shows a perspective view of a medical instrument of a further preferred embodiment in the form of medical forceps.
Figure 18:
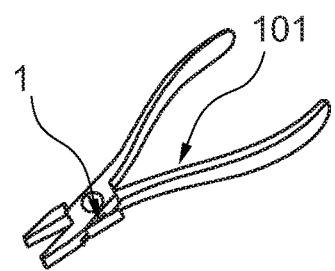
FIG. 18 shows a perspective view of a medical instrument of a further preferred embodiment in the form of medical forceps.
Figure 19:
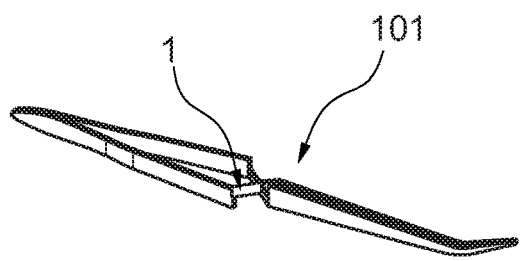
FIG. 19 shows a perspective view of a medical instrument of a further preferred embodiment in the form of medical forceps.

FIGS. 14 to 19 show in a perspective view or top view various medical instruments 101 of preferred embodiments with a transponder installation module 1. Specifically, FIG. 14 shows a medical punch with transponder installation module 1, FIG. 15 shows medical or surgical scissors with the transponder installation module 1, FIG. 16 shows a further medical punch with the transponder installation module 1, FIG. 17 shows medical forceps with transponder installation module 1, FIG. 18 shows further medical forceps with transponder installation module 1, and FIG. 19 shows medical tweezers with transponder installation module 1. The transponder installation module 1, in particular of one embodiment, can thus be inserted into many different medical instruments 101, which in particular have a standardized prepared depression 103 or opening.

Figure 20:
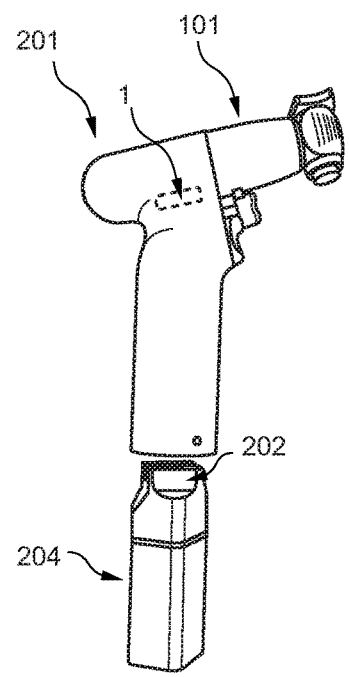
FIG. 20 shows a perspective view of a medical transponder system of a first preferred embodiment.
Figure 21:
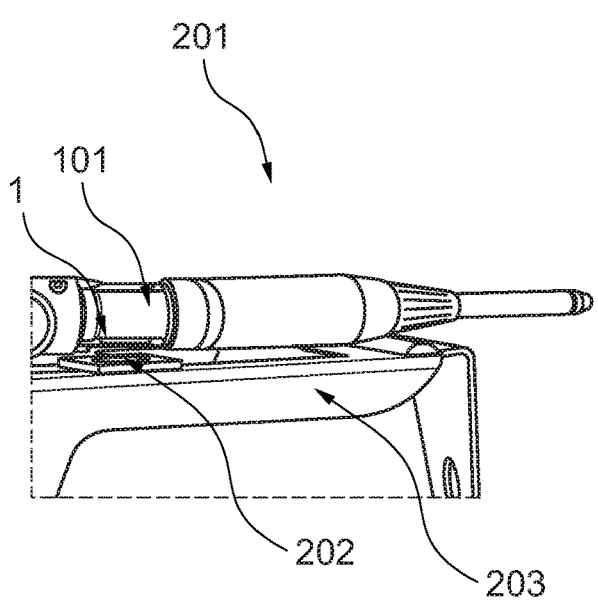
FIG. 21 shows a perspective view of a medical transponder system of a further preferred embodiment.

FIGS. 20 and 21 each show a medical transponder system/medical transponder communication system 201 according to the invention of a preferred embodiment with a transponder installation module 1, which is used in a medical instrument 101 according to the invention, and a compatible reading and writing device 202. Alternatively, of course, only a reading device or only a writing device may be used.

In FIG. 20, the transponder installation module 1 is inserted in an interior of a handpiece of a medical instrument 101. Since the handpiece is made of metal as material, the transponder 2 cannot be read from the outside, but a reading and/or writing activity is required inside the handpiece. This is realized by a reading and writing device 202 being arranged in or on a surface of the accumulator 204 of the medical instrument. When the accumulator is inserted into the interior of the handpiece and is firmly inserted, the transponder is written and/or read by the reading and writing device 202 located in the interior of the handpiece. It may also be provided that the reading and writing device 202 starts writing and/or reading when the accumulator is removed.

FIG. 21 shows a transponder system 201 of a further embodiment. This has a holding system 203 for bringing the medical instrument 101 with the transponder installation module 1 inserted into a predetermined arrangement with respect to the reading and writing device 202 and then also for holding it in this position and orientation during communication, so that secure and reliable transmission is ensured.

Figure 22:
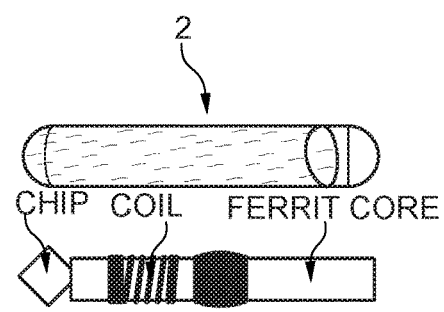
FIG. 22 shows a top view of a transponder in the form of a glass tag.

FIG. 22 shows a top view of a glass tag 2 with an RFID chip, a rod-shaped ferrite core and a coil wound around it, wherein the sheathing has been omitted for better viewing in the lower part of FIG. 22.

The invention claimed is:
1. A medical instrument comprising:
an instrument body having a prepared depression or opening in an instrument body surface, and
a transponder installation module comprising:
a transponder;
a housing having an upper side and a lower side in which the transponder is accommodated and which is provided and configured to be installed or inserted into the prepared depression or opening of the medical instrument with the lower side facing in a direction of the prepared depression or opening, so that the lower side is set back relative to the upper side of the transponder installation module and the instrument body surface; and
a screen which is signal-impermeable for electromagnetic waves with a screen opening that is signal-permeable wherein the entire screen and screen opening are located, with respect to a direction extending from the upper side of the housing to the lower side of the housing, behind the upper side of the housing and between the upper side of the housing and the transponder,
the transponder being spaced apart from and set back from the screen toward the lower side of the transponder installation module, and
wherein the housing and the screen opening define a path that is signal-permeable to electromagnetic waves, the path extending fully from the upper side of the housing to the transponder.

2. The medical instrument according to claim 1, wherein the transponder is an RFID transponder.

3. The medical instrument according to claim 1, wherein the transponder is a glass transponder.

4. The medical instrument according to claim 1, wherein the screen is configured in several parts and comprises a first screen segment and a second screen segment, the first screen segment and the second screen segment configured to engage each other in a form-fitting manner via a latching mechanism, wherein the first screen segment and the second screen segment define the screen opening between them.

5. The medical instrument according to claim 4, wherein the first screen segment and the second screen segment are identical components in a U-shaped configuration, and a latch projection extending orthogonally to a longitudinal axis of the screen opening is configured at a first free end, and a latch depression extending orthogonally to the longitudinal axis of the screen opening is configured at a second free end.

6. The medical instrument according to claim 5, wherein the latch projection and the latch depression point in the same direction.

7. The medical instrument according to claim 4, wherein the first screen segment and the second screen segment prevent insertion and removal of the transponder from the housing in the form-fitting latching engagement.

8. The medical instrument according to claim 1, wherein the housing comprises a first housing part and a second housing part, between which the transponder is received in a fixed position, and the screen mechanically fixes the first housing part to the second housing part.

9. The medical instrument according to claim 8, wherein the second housing part is U-shaped with a housing base and two housing pins that are adjoining, parallel, and cylindrical, the housing pins configured to be inserted in parallel, complementary receptacles formed in the first housing part in the manner of a form-fitting plug-in connection, and the screen form-fittingly engages around the first housing part and the second housing part and fixes the first housing part and the second housing part against each other.

10. The medical instrument according to claim 8, wherein the second housing part is U-shaped with a semi-cylindrical housing base.

11. The medical instrument according to claim 1, wherein:
the transponder has a cylindrical shape with a first longitudinal axis extending perpendicular to the direction extending from the upper side of the housing to the lower side of the housing,
the screen opening is configured to be elongated or slit-shaped or slot-shaped and comprises a second longitudinal axis extending perpendicular to the direction extending from the upper side of the housing to the lower side of the housing, and
the first longitudinal axis is arranged parallel to and spaced from the second longitudinal axis.

12. The medical instrument according to claim 11, wherein:
the housing has a plane of symmetry that is perpendicular to the direction extending from the upper side of the housing to the lower side of the housing, and
the upper side and the lower side are configured to be flat and extend perpendicular to the direction extending from the upper side of the housing to the lower side of the housing.

13. The medical instrument according to claim 11, wherein the upper side and the lower side are configured to be planar and parallel to each other.

14. The medical instrument according to claim 11, wherein the first longitudinal axis is symmetrical relative to the second longitudinal axis.

15. The medical instrument according to claim 1, wherein the housing is made of thermoplastic material and the screen is made of metal.

16. The medical instrument according to claim 1, wherein the housing is made of polypropylene.

17. The medical instrument according to claim 1, wherein at least one of:
the transponder installation module is configured to be assembled without tools; and
the transponder installation module is insertable into and removable from the prepared depression or opening without tools,
wherein the housing and the prepared depression or opening are matched to each other such that the housing forms a press fit in an inserted state.

18. The medical instrument according to claim 1, wherein:
the upper side of the housing extends in a plane that is perpendicular to the direction extending from the upper side of the housing to the lower side of the housing;
the lower side of the housing is offset in the plane from the upper side of the housing to be smaller, in the plane, than the upper side of the housing; and
the entire screen is offset in the plane from the upper side of the housing to be smaller, in the plane, than the upper side of the housing.

19. The medical instrument according to claim 1, wherein:
the upper side of the housing extends in a plane that is perpendicular to the direction extending from the upper side of the housing to the lower side of the housing;
the lower side of the housing is offset in the plane from the upper side of the housing to be smaller, in the plane, than the upper side of the housing;

the lower side of the housing comprises:
- a first housing part defining a hole extending along a first axis parallel that is parallel to the plane, with the transponder being inserted along the first axis into the hole, and
- a second housing part configured be secure along the first axis to the first housing part to cover the hole and enclose the transponder;

the screen comprise a first screen segment and a second screen segment that are configured to be secured to surround a respective portion of the first housing part and a respective portion of the second housing part and hold the first housing part to the second housing part; and the respective portion of the first housing part and the respective portion of the second housing part are located in the screen opening.

20. A medical transponder communication system comprising:
- a medical instrument according to claim 1; and
- a reading and/or writing device that is signal-technically coupleable to the transponder,
- the reading and/or writing device adapted to hold or temporarily fix the medical instrument with the transponder installation module in a predetermined position and/or orientation relative to the reading and/or writing device, in which a signal transmission between the transponder and the reading and/or writing device is enabled.

21. The medical transponder communication system according to claim 20, wherein the reading and/or writing device comprises or is an instrument holder.

* * * * *